(12) United States Patent
Armacost et al.

(10) Patent No.: US 10,213,314 B2
(45) Date of Patent: *Feb. 26, 2019

(54) FEMORAL COMPONENT FOR AN IMPLANTABLE HIP PROSTHESIS

(71) Applicant: DEPUY SYNTHES PRODUCTS, INC., Raynham, MA (US)

(72) Inventors: John M. Armacost, Warsaw, IN (US); Ryan C. Keefer, Warsaw, IN (US); Jeffrey A. McAnelly, Columbia City, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/665,658

(22) Filed: Aug. 1, 2017

(65) Prior Publication Data

US 2017/0325963 A1 Nov. 16, 2017

Related U.S. Application Data

(60) Continuation of application No. 14/995,843, filed on Jan. 14, 2016, now Pat. No. 9,717,597, which is a division of application No. 13/829,026, filed on Mar. 14, 2013, now Pat. No. 9,271,839.

(51) Int. Cl.
*A61F 2/36* (2006.01)
*A61F 2/30* (2006.01)

(52) U.S. Cl.
CPC .. *A61F 2/3662* (2013.01); *A61F 2002/30013* (2013.01); *A61F 2002/30014* (2013.01); *A61F 2002/30069* (2013.01); *A61F 2002/365* (2013.01); *A61F 2310/00023* (2013.01); *A61F 2310/00029* (2013.01)

(58) Field of Classification Search
CPC .... A61F 2/3601; A61F 2/3607; A61F 2/3609; A61F 2/3662; A61F 2/4059
See application file for complete search history.

(56) References Cited

U.S. PATENT DOCUMENTS

| | | | |
|---|---|---|---|
| 4,164,794 A | 8/1979 | Spector et al. | |
| 4,227,265 A | 10/1980 | Frey | |
| 4,351,069 A | 9/1982 | Ballintyn et al. | |

(Continued)

FOREIGN PATENT DOCUMENTS

| | | |
|---|---|---|
| DE | 3442845 A1 | 6/1985 |
| DE | 10029859 A1 | 9/2001 |

(Continued)

OTHER PUBLICATIONS

Long, Marc et al., "Titanium alloys in total joint replacement—a materials science perspective," Biomaterials, 19, (1998), 1621-1639.

(Continued)

*Primary Examiner* — Brian Dukert
(74) *Attorney, Agent, or Firm* — Barnes & Thornburg LLP (57) ABSTRACT

An orthopedic prosthesis for use in a hip replacement surgery includes an implantable stem component. The implantable stem component includes a core and a shell extending over the core. The shell includes a polymeric material and is configured to receive a femoral head component. Metal foam may extend over a portion of the shell.

11 Claims, 6 Drawing Sheets

(56) References Cited

U.S. PATENT DOCUMENTS

| | | |
|---|---|---|
| 4,756,862 A | 7/1988 | Spector et al. |
| 4,808,186 A | 2/1989 | Smith |
| 4,851,008 A | 7/1989 | Johnson |
| 4,878,919 A | 11/1989 | Pavlansky et al. |
| 4,986,834 A | 1/1991 | Smith et al. |
| 4,990,161 A | 2/1991 | Kampner |
| 5,152,798 A | 10/1992 | Kranz |
| 5,181,930 A | 1/1993 | Dumbleton et al. |
| 5,314,492 A | 5/1994 | Hamilton et al. |
| 5,316,550 A | 5/1994 | Forte |
| 5,336,265 A | 8/1994 | Serbousek et al. |
| 5,433,750 A | 7/1995 | Gradinger et al. |
| 5,443,513 A | 8/1995 | Moumene et al. |
| 5,480,449 A | 1/1996 | Hamilton et al. |
| 5,514,184 A | 5/1996 | Doi et al. |
| 5,545,227 A | 8/1996 | Davidson et al. |
| 5,549,702 A | 8/1996 | Ries et al. |
| 5,591,233 A | 1/1997 | Kelman et al. |
| 5,702,448 A | 12/1997 | Buechel et al. |
| 5,735,905 A * | 4/1998 | Parr .................. A61F 2/3609 623/23.11 |
| 5,834,113 A | 11/1998 | Shalaby et al. |
| 6,066,176 A | 5/2000 | Oshida |
| 6,121,172 A | 9/2000 | Marcolongo et al. |
| 6,228,123 B1 | 5/2001 | Dezzani |
| 6,296,667 B1 | 10/2001 | Johnson et al. |
| 6,312,473 B1 | 11/2001 | Oshida |
| 6,409,852 B1 | 6/2002 | Lin et al. |
| 6,602,293 B1 | 8/2003 | Biermann et al. |
| 6,626,948 B2 | 9/2003 | Storer et al. |
| 6,656,226 B2 | 12/2003 | Yoon |
| 6,695,884 B1 | 2/2004 | Townley |
| 6,719,793 B2 | 4/2004 | McGee |
| 6,887,278 B2 | 5/2005 | Lewallen |
| 6,913,623 B1 | 7/2005 | Zhu |
| 7,141,073 B2 | 11/2006 | May et al. |
| 7,947,084 B2 | 5/2011 | Link |
| 8,088,169 B2 * | 1/2012 | Dorr .................. A61F 2/30767 623/23.32 |
| 8,906,108 B2 | 12/2014 | Armacost et al. |
| 9,271,839 B2 | 3/2016 | Armacost et al. |
| 9,717,597 B2 | 8/2017 | Armacost et al. |
| 9,907,657 B2 | 3/2018 | Fonte et al. |
| 2002/0016635 A1 | 2/2002 | Despres, III et al. |
| 2002/0049501 A1 | 4/2002 | Storer et al. |
| 2004/0102854 A1 | 5/2004 | Zhu |
| 2004/0172138 A1 | 9/2004 | May et al. |
| 2005/0119759 A1 | 6/2005 | Tuke et al. |
| 2006/0184250 A1 | 8/2006 | Bandoh et al. |
| 2006/0240064 A9 | 10/2006 | Hunter et al. |
| 2007/0093912 A1 | 4/2007 | Borden |
| 2007/0150068 A1 | 6/2007 | Dong et al. |
| 2007/0219641 A1 | 9/2007 | Dorr et al. |
| 2008/0039941 A1 | 2/2008 | Steinberg |
| 2008/0167723 A1 | 7/2008 | Acker et al. |
| 2008/0200990 A1 | 8/2008 | McTighe et al. |
| 2008/0243264 A1 | 10/2008 | Fonte |
| 2008/0255675 A1 | 10/2008 | Sidebotham |
| 2009/0005868 A1 | 1/2009 | Gundlapalli et al. |
| 2009/0076508 A1 | 3/2009 | Weinans et al. |
| 2009/0162235 A1 | 6/2009 | Kita et al. |
| 2009/0234459 A1 | 9/2009 | Sporring et al. |
| 2010/0174377 A1 | 7/2010 | Heuer |
| 2010/0312354 A1 | 12/2010 | Bandoh et al. |
| 2012/0010720 A1 | 1/2012 | Dickerson |
| 2012/0022662 A1 | 1/2012 | Conway et al. |
| 2012/0125896 A1 | 5/2012 | Vargas et al. |
| 2012/0196147 A1 | 8/2012 | Rabiei |
| 2013/0338789 A1 | 12/2013 | Armacost et al. |
| 2014/0107801 A1 | 4/2014 | Armacost et al. |
| 2014/0277557 A1 | 9/2014 | Armacost et al. |
| 2017/0246001 A1 | 8/2017 | Conway et al. |
| 2017/0367829 A1 | 12/2017 | Choudhury et al. |

FOREIGN PATENT DOCUMENTS

| | | |
|---|---|---|
| EP | 0375599 A2 | 6/1990 |
| EP | 0484082 A1 | 5/1992 |
| EP | 2777622 | 9/2014 |
| FR | 2839641 A1 | 11/2003 |
| JP | 0663067 A | 3/1994 |
| JP | 2004537370 A | 12/2004 |
| JP | 2007151805 A | 6/2007 |
| JP | 2012115356 A | 6/2012 |
| WO | 1983002555 A1 | 8/1983 |
| WO | 9306793 | 4/1993 |
| WO | 2002013730 A2 | 2/2002 |
| WO | 2011005126 A1 | 1/2011 |
| WO | 2012065068 A1 | 5/2012 |

OTHER PUBLICATIONS

European Search Report for European Application No. 13171799. 3-1654, dated Oct. 4, 2013, 4 pages.

European Search Report for European Application No. 14156387. 4.-1654, dated May 14, 2014, 6 pages.

Chapter 52, Strain Distribution in the Proximal Femur After Cementless Implantation of Hip Replacements, Mathys et al., Biomechanics:Current Interdisciplinary Research, pp. 371-376.

Von Hasselbach C, Bombelli R, The isoelastic RM hip endoprosthesis, OP-Journal. 6(2): 29-37 (1990).

English translation of Notification of Reasons for Refusal in Japanese Patent Application No. 2014-050097, completed Jan. 9, 2018.

Partial European Search Report for European Patent Application No. 14197339.6, completed Apr. 30, 2015, 7 pages.

* cited by examiner

FEMORAL COMPONENT FOR AN IMPLANTABLE HIP PROSTHESIS

CROSS-REFERENCE TO RELATED APPLICATIONS

This application is a continuation of U.S. patent application Ser. No. 14/995,843, which was filed on Jan. 14, 2016 and is now issued as U.S. Pat. No. 9,717,597, which is a divisional of U.S. patent application Ser. No. 13/829,026, which was filed on Mar. 14, 2013 and is now issued as U.S. Pat. No. 9,271,839, and which are incorporated herein by reference.

TECHNICAL FIELD

The present disclosure relates generally to orthopaedic prostheses, and particularly to orthopaedic prostheses for use in hip replacement surgery.

BACKGROUND

Joint arthroplasty is a well-known surgical procedure by which a diseased and/or damaged natural joint is replaced by a prosthetic joint. The prosthetic joint may include a prosthesis that is implanted into one or more of the patient's bones. Many hip prostheses include a femoral prosthesis that is implanted into a patient's femur. A femoral prosthesis typically includes an elongated stem component that is received in the medullary canal of the patient's femur and a spherically-shaped head component that bears against the patient's acetabulum or a prosthetic replacement acetabular cup.

Many femoral prostheses are formed from metallic materials or a combination of metallic and polymeric materials. According to Wolff's law, a patient's bone tissue will remodel in proportion to the stress applied it. Because elongated stem components formed from metal typically have an elastic modulus greater than the elastic modulus of the patient's bone, metallic stem components may shield the patient's bone from stress such that the proximal femoral bone does not remodel to an effective degree, possibly resulting in a loss of support for the implant and/or implant failures.

SUMMARY

According to one aspect of the disclosure, an orthopaedic hip prosthesis is disclosed. The orthopaedic hip prosthesis includes a femoral head component including a spherical surface shaped to engage a prosthetic acetabular component and a femoral stem component. The stem component has a first shell including a neck configured to be secured to the femoral head component and an elongated body extending distally from the neck. The first shell includes a polymeric material. The stem component also includes a core that is positioned in the first shell, and the core is formed from a material having a high tensile strength and a high elastic modulus. The core includes a first core body extending into the neck of the first shell and a second core body extending into the elongated body of the first shell. A second shell extends over a proximal section of the elongated body of the first shell. The second shell is formed from a metallic foam.

In some embodiments, the first shell may include a shoulder having a distal surface, and the second shell may include a proximal end that is engaged with the distal surface of the shoulder.

In some embodiments, the second core body of the core may have a medial surface and a lateral surface positioned opposite the medial surface, and the second shell may have a medial surface and a lateral surface positioned opposite the medial surface. When the orthopaedic hip prosthesis is viewed in a transverse plane, the first shell and the second shell may define a first thickness between a medial-most point of the medial surface of the second shell and a medial-most point of the medial surface of the first core body and a second thickness between a lateral-most point of the lateral surface of the second shell and a lateral-most point of the lateral surface of the first core body. The first thickness may be less than the second thickness.

In some embodiments, when the orthopaedic hip prosthesis is viewed in the transverse plane, the medial surface of the first core body may be convex and the lateral surface of the first core body is convex.

In some embodiments, when the orthopaedic hip prosthesis is viewed in the transverse plane, the medial surface of the first core body may be defined by a first radius and the lateral surface of the first core body may be defined by a second radius that is greater than the first radius.

Additionally, in some embodiments, the transverse plane may be a first transverse plane extending through the first shell, the second shell, and the core, and the first shell may have a medial surface and a lateral surface positioned opposite the medial surface. When the orthopaedic hip prosthesis is viewed in a second transverse plane extending through the orthopaedic hip prosthesis distal of the second shell, a third thickness may be defined between a medial-most point of the medial surface of the first shell and a medial-most point of the medial surface of the first core body. The third thickness may be greater than the first thickness.

In some embodiments, the femoral head component may include a tapered bore, and the neck of the first shell may include a tapered post configured to be received in the tapered bore of the femoral head component.

In some embodiments, the femoral head component may include a body including the spherical surface. The femoral head component may also include a polymeric insert positioned in the body, and the insert may have the tapered bore defined therein.

In some embodiments, the metallic foam shell may be shaped to engage a surgically-prepared proximal end of a patient's femur. Additionally, the first shell may be formed from a metal-polymer composite material. In some embodiments, the material of the core may be selected from a group consisting of a cobalt-chromium alloy and a titanium alloy.

According to another aspect, an orthopaedic hip prosthesis is disclosed. The orthopaedic hip prosthesis includes an implantable distal stem component including a core formed from a material having a high tensile strength and a high elastic modulus and a shell extending over the core. The shell including a tapered post configured to be received in a tapered bore of an implantable head component. The shell includes a polymeric material.

In some embodiments, when the orthopaedic hip prosthesis is viewed in a transverse plane extending through the shell and the core, a first thickness may be defined between a medial-most point of the shell and a medial-most point of a medial surface of the core, and a second thickness may be defined between a lateral-most point of the shell and a lateral-most point of a lateral surface of the core. The first thickness may be less than the second thickness.

In some embodiments, the shell may include a sheath extending over a proximal end of the core and a cover layer extending distally from the sheath. The cover layer may engage only a lateral surface of a distal end of the core.

Additionally, in some embodiments, the shell may be formed from a metal-polymer composite material. In some embodiments, the core may be formed from cobalt-chromium alloy.

In some embodiments, the shell may be a first shell including an elongated body, and the implantable distal stem component may include a second shell extending over a proximal section of the elongated body. The second shell may be formed from a metallic foam. In some embodiments, the second shell may be formed from titanium. In some embodiments, the second shell is formed from cobalt-chromium alloy.

According to another aspect, an orthopaedic hip prosthesis includes an implantable distal stem component. The stem component includes a first shell, a core positioned in the first shell, and a second shell. The first shell includes a tapered post configured to be received in a tapered bore of an implantable head component and an elongated body extending distally from the tapered post. The first shell is also formed from a metal-polymer composite material. The elongated body of the first shell includes a distal section shaped to engage the surgically-prepared proximal end of a patient's femur distal of the second shell.

The core is formed from a material having a high tensile strength and a high elastic modulus. The core includes a first core body extending into the tapered post of the first shell and a second core body extending into the elongated body of the first shell. The second shell extends over a proximal section of the elongated body of the first shell, and the second shell is formed from a metallic foam and including a porous outer surface shaped to engage a surgically-prepared proximal end of a patient's femur.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
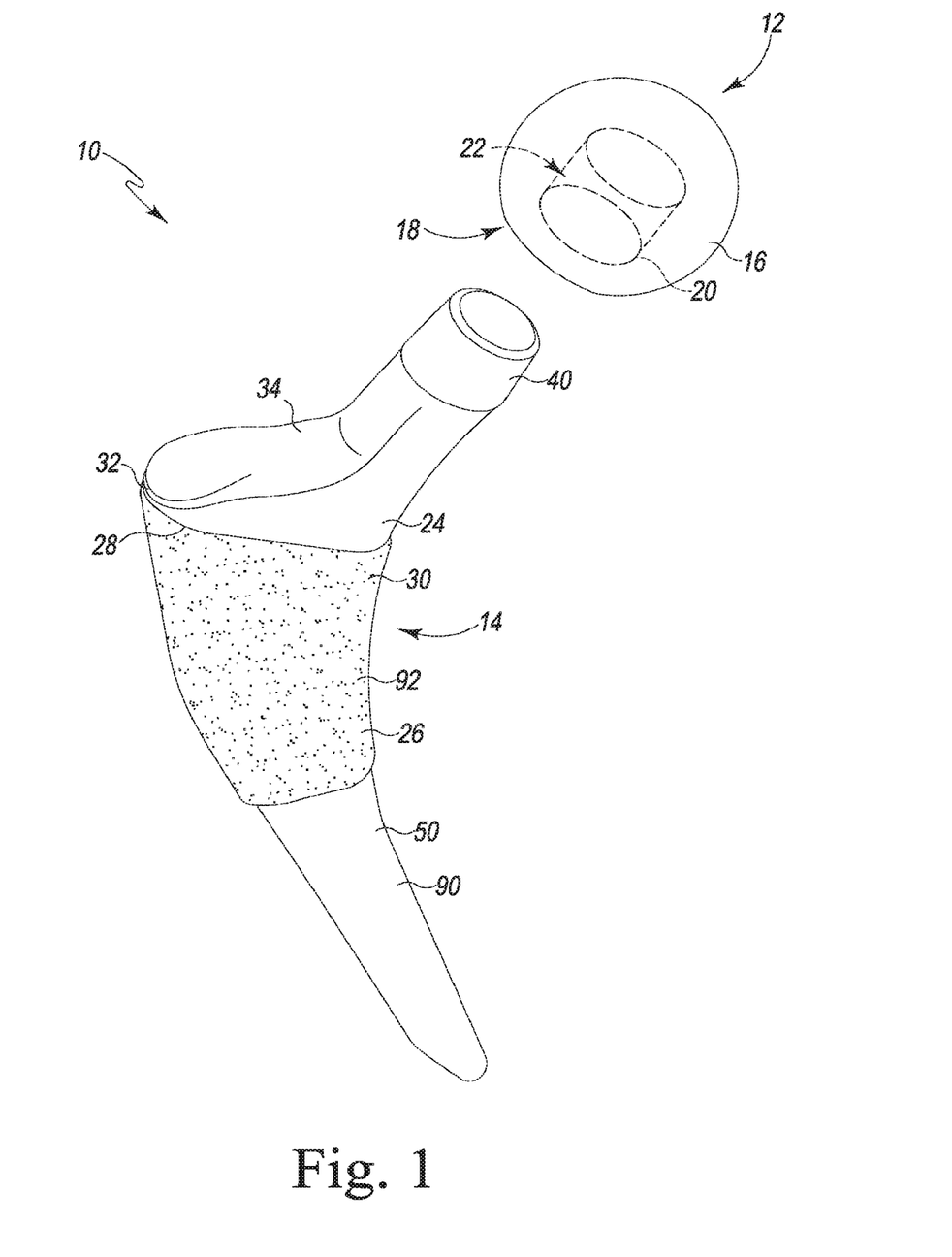
FIG. 1 is a perspective view of one embodiment of an implantable hip prosthesis.

Referring to FIG. 1, an orthopaedic prosthesis is illustratively embodied as an implantable hip prosthesis 10 for use during a hip replacement procedure. The implantable hip prosthesis 10 (hereinafter prosthesis 10) includes a head component 12 and an elongated stem component 14 that is configured to be inserted into an intramedullary canal of a patient's surgically-prepared (e.g., reamed and/or broached) femur. The head component 12 includes a spherical outer surface 16 configured to engage a patient's natural acetabulum (not shown) or a prosthetic acetabular cup implanted into the patient's pelvic bone. The head component 12 also includes a distal surface 18 having an opening 20 defined therein, and an inner wall 164 (see FIG. 2) extends inwardly from the opening 20 to define a bore 22 in the head component 12.

The stem component 14 may be provided in a number of different configurations in order to fit the needs of a given patient's anatomy. In particular, the stem component 14 may be configured in various different lengths to conform to the patient's anatomy (e.g. a relatively long stem component 14 for use with a long femur, a relatively short stem for use with a short femur, etcetera). As shown in FIG. 1, the stem component 14 includes a shell or casing 24 and a shell 26 that is secured to the casing 24. The casing 24 has a shoulder 28 that is engaged with a proximal end 30 of the shell 26. The shoulder 28 defines a collar 32 that has a neck 34 extending proximally and medially therefrom.

The neck 34 is configured to be coupled to the head component 12. In the illustrative embodiment, the bore 22 of the head component 12 is tapered, and the neck 34 of the stem component 14 includes a tapered post 40 that is received in the tapered bore 22. When the tapered post 40 is seated in the tapered bore 22, the head component 12 is taper locked onto the stem component 14. It should be appreciated that in other embodiments the neck and the head component may be configured to be press fit or secured together by other mechanical fastening means.

Figure 2:
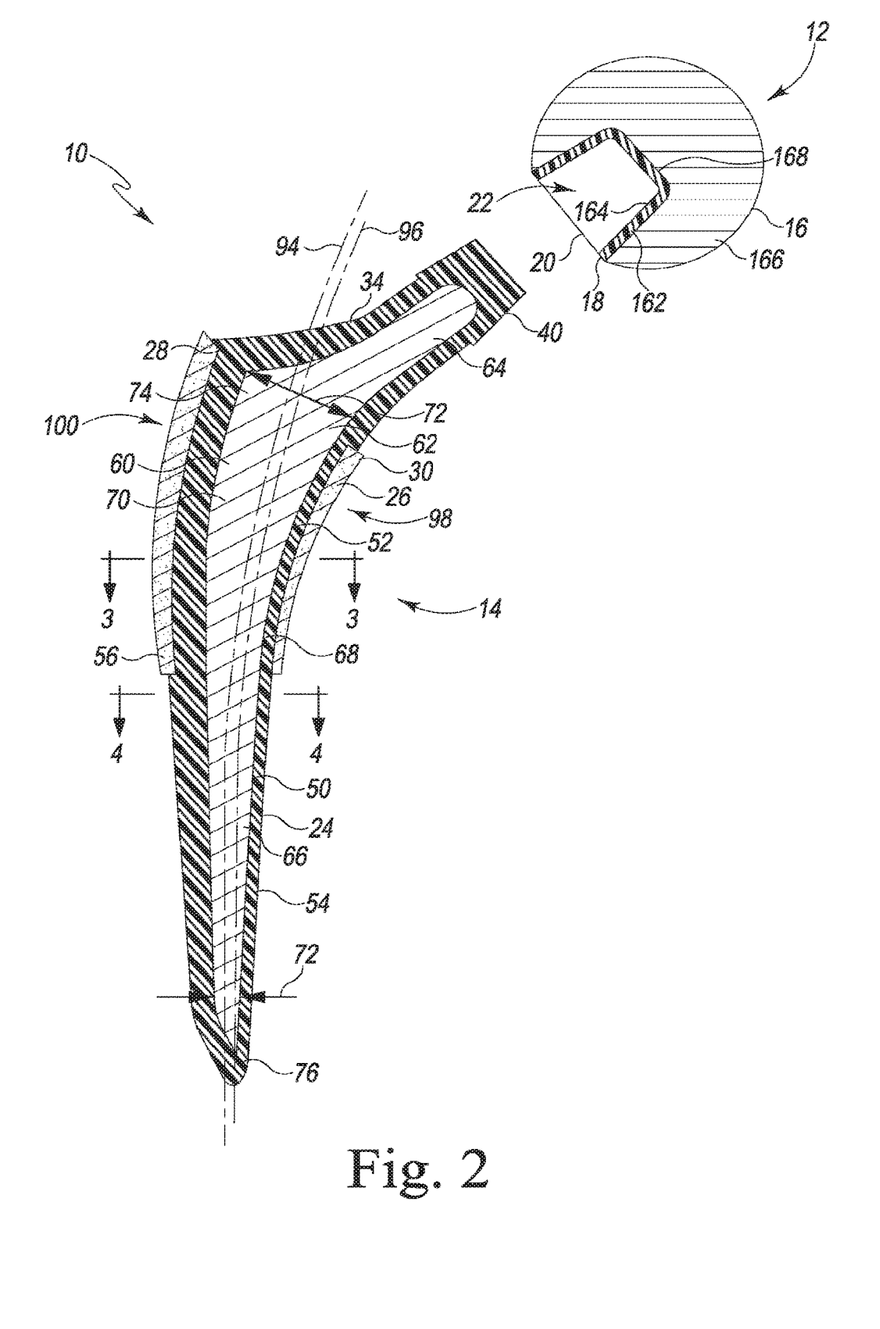
FIG. 2 is a cross-sectional elevation view of the implantable hip prosthesis of FIG. 1.

The casing 24 also includes an elongated body 50 that extends distally from the collar 32. As shown in FIG. 2, the elongated body 50 includes a proximal section 52 that is positioned in the shell 26 and a distal section 54 that extends outwardly from the distal end 56 of the shell 26. In the illustrative embodiment, the neck 34, the collar 32, and the elongated body 50 are formed as a monolithic structure (e.g., a single molded or cast part). It should be appreciated that in other embodiments the components of the casing 24 (e.g., the neck 34, the collar 32, and the body 50) may be formed as separate components secured to one another by a mechanical fastener (e.g., screw, bolt, taper fit, etc.), adhesive, or other suitable fastener.

As shown in FIG. 2, the casing 24 of the stem component 14 encases an inner core 60. In the illustrative embodiment, the inner core 60 is sized and shaped to meet the minimum strength requirements of the prosthesis 10, while the casing 24 and the shell 26 cooperate to define an external geometry of the stem component 14 necessary to fit into the intramedullary canal of the patient's femur. The minimum strength of the core is determined in accordance with International Organization for Standardization Standard No. 7206-4:2010 "IMPLANTS FOR SURGERY—PARTIAL AND TOTAL HIP JOINT PROSTHESES—PART 4: DETERMINATION OF ENDURANCE PROPERTIES AND PERFORMANCE OF STEMMED FEMORAL COMPONENTS" and Standard No. 7206-6:1992 "IMPLANTS FOR SURGERY—PARTIAL AND TOTAL HIP JOINT PROSTHESES—PART 6: DETERMINATION OF ENDURANCE PROPERTIES OF HEAD AND NECK REGION OF STEMMED FEMORAL COMPONENTS." The inner core 60 of the stem component 14 includes a core body 62 having a proximal segment 64 and a distal segment 66. The proximal segment 64 extends into the neck 34 of the casing 24 to reinforce the tapered post 40, while the elongated distal segment 66 extends into the elongated body 50 to reinforce that section of the casing 24.

The inner core 60 is formed as a monolithic structure (e.g., a single molded or cast part). It should be appreciated that in other embodiments the components of the core 60 (e.g., the segments 64, 66) may be formed as separate components secured to one another by a mechanical fastener (e.g., screw, bolt, taper fit, etc.), adhesive, or other suitable fastener. In the illustrative embodiment, the inner core 60 is formed from an implant grade metallic material having a high tensile strength and a high elastic modulus (i.e., a high material stiffness). As used herein, the term "high tensile strength" refers to a tensile strength that is greater than 650 MPa. Additionally, as used herein, the term "high elastic modulus" refers to an elastic modulus or modulus of elasticity that is greater than or equal to 100 GPa. In the illustrative embodiment, the core 60 is formed from cobalt-chromium alloy ("CoCr") having a minimum ultimate tensile strength of 650 MPa and an elastic modulus of approximately 195 GPa. It should be appreciated that in other embodiments the core 60 may be formed any material having a high tensile strength and a high elastic modulus, including, for example, a titanium alloy such as Ti-6Al-4V, which has a minimum ultimate tensile strength of 750 MPa and an elastic modulus of approximately 105 GPa.

The core body 62 of the inner core 60 lies generally in the coronal plane of a patient's body when the prosthesis 10 is secured to the patient's femur. As shown in FIG. 2, the elongated distal segment 66 of the core body 62 includes a medial surface 68 and a lateral surface 70 positioned opposite the medial surface 88. When the core 60 is viewed in the coronal plane, the core elongated distal segment 66 has a thickness 72 at its proximal end 74. As shown in FIG. 2, the thickness 72 is defined between the surfaces 68, 70.

The distal segment 66 of the core body 62 has another thickness 78 at its distal end 76 when the core 60 is viewed in the coronal plane. The thickness 78, like the thickness 72, is defined between the surfaces 68, 70 adjacent to the distal end 76. In the illustrative embodiment, the thickness 78 is less than the thickness 72. In that way, the core body 62 tapers to decrease in thickness between the proximal end 74 and the distal end 76.

Figure 3:
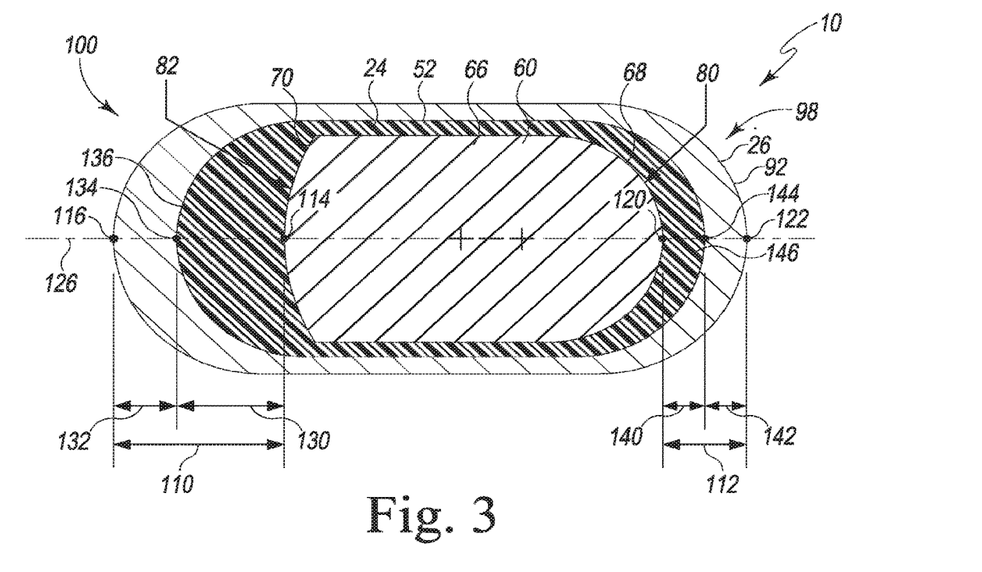
FIG. 3 is a cross-sectional view of the implantable hip prosthesis taken along the line 3-3 in FIG. 2.
Figure 4:
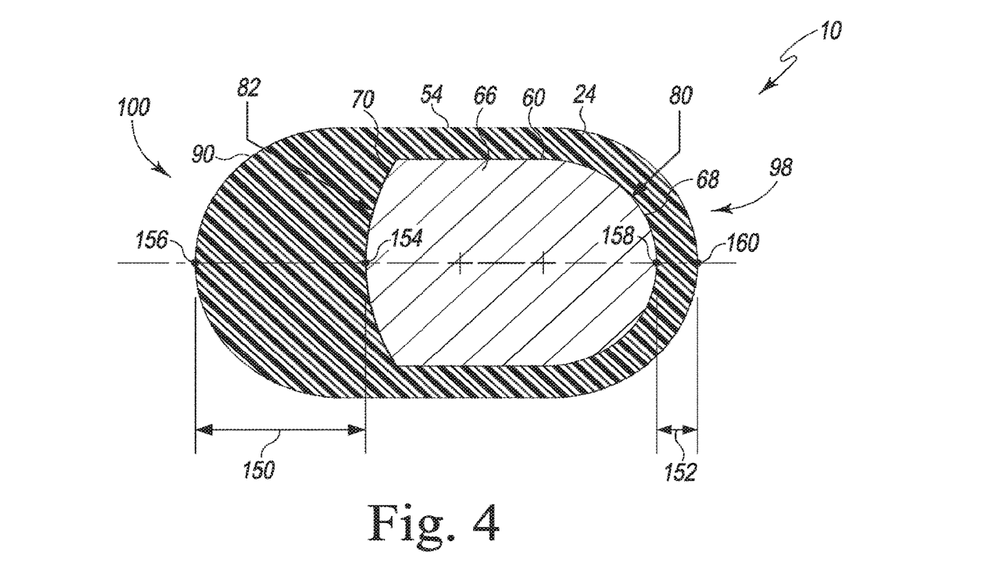
FIG. 4 is a cross-sectional view of the implantable hip prosthesis taken along the line 4-4 in FIG. 2.

As shown in FIGS. 3-4, the medial surface 68 and the lateral surface 70 of the distal segment 66 are convex surfaces. As described in greater detail below, the medial surface 68 is defined by a radius 80 that decreases in magnitude as the medial surface 68 extends from the proximal end 74 of the distal segment 66 to the distal end 76. The lateral surface 70 is defined by a radius 82 that, like the radius 80, decreases in magnitude as the lateral surface 70 extends from the proximal end 74 of the distal segment 66 to the distal end 76. While the radii 80, 82 decrease in magnitude, the magnitude of the radius 82 of the lateral surface 70 is greater than the magnitude of the radius 80 of the medial surface 68.

As described above, the casing 24 encases the inner core 60. As shown in FIG. 2, the inner core 60 is completely surrounded by the casing 24. It should be appreciated that in other embodiments portions of the inner core 60 may be exposed or extend from the casing 24. In the illustrative embodiment, the casing 24 is molded over the inner core 60 and is formed from a metal polymer composite material having a low elastic modulus. As used herein, a "low elastic modulus" refers to an elastic modulus or modulus of elasticity similar to that of a patient's natural femur, which is between about 10 GPa and 20 GPa.

In the illustrative embodiment, the casing 24 is formed from a composite reinforced polymer such as, for example, carbon-fiber reinforced polyetheretherketone ("PEEK"). The composite has an elastic modulus of approximately 21.5 GPa and an ultimate tensile strength of approximately 223 MPa. In that way, the casing 24 has an elastic modulus that is closer to that of a patient's femur. It should be appreciated that in other embodiments the casing 24 may be formed any composite or polymeric material having a low elastic modulus, such as, for example, a glass-filled polymer such as glass-filled PEEK, a non-reinforced polymer such as neat PEEK, or other reinforced or non-reinforced polymer.

As described above, the stem component 14 of the prosthesis 10 also includes a shell 26 that is secured to the proximal section 52 of the casing 24. The shell 26 is formed from a metallic foam matrix having a low elastic modulus. In the illustrative embodiment, the shell 26 is formed from a foam matrix of titanium having an elastic modulus of approximately 10 GPa and an ultimate tensile strength of the foam matrix of titanium is approximately 35 MPa. In that way, the shell 26 has an elastic modulus that is closer to that of a patient's femur. It should be appreciated that in other embodiments the shell 26 may be formed any metallic foam matrix having a low elastic modulus, such as, for example, a CoCr foam matrix having an elastic modulus of approximately 19 GPa, a CoCr alloy foam matrix, a titanium foam alloy matrix, or other foam matrix.

As shown in FIG. 1, the casing 24 and the shell 26 have outer surfaces 90, 92, respectively. The outer surfaces 90, 92 define the external geometry of the prosthesis 10. As such, the outer surfaces 90, 92 engage the portion of the patient's femur defining the intramedullary canal when the prosthesis 10 is inserted into the proximal end of the patient's surgically-prepared femur. In the illustrative embodiment, the outer surface 92 of the shell 26 is porous to enable bone ingrowth fixation, and the outer surface 90 of the casing 24 is non-porous. It should be appreciated that in other embodiments the casing 24 may also be porous. It should also be appreciated that in other embodiments the stem component 14 may not include the foam shell 26. In such embodiments, the outer surface of the casing may define the entire external geometry of the stem component 14.

As shown in FIG. 2, the elongated body 50 of the casing 24, the distal segment 66 of the inner core 60, and the shell 26 cooperate to define a longitudinal axis 94 of the stem component 14. The distal segment 66 of the inner core 60 has a longitudinal axis 96 that is offset from the axis 94 of the stem component 14. In the illustrative embodiment, the axis 96 is offset in the medial direction from the axis 94 such that the distal segment 66 of the inner core 60 is biased toward the medial side 98 of the stem component 14 and away from the lateral side 100 of the stem component 14. Additionally, in the proximal section 52 of the casing 24, the thickness of the casing 24 and the shell 26 on the lateral side 100 of the stem component 14 is greater than the thickness of the casing 24 and the shell 26 on the medial side 98 of the stem component 14.

For example, as shown in FIG. 3, the casing 24 and the shell 26 have a combined lateral thickness 110 and a combined medial thickness 112 when viewed in a transverse plane extending through the proximal section 52 of the casing 24. The lateral thickness 110 is defined between a lateral-most point 114 of the lateral surface 70 of the inner core 60 and a lateral-most point 116 of an outer surface 92 of the shell 26. The medial thickness 112 of the casing 24 is defined between a medial-most point 120 of the medial surface 68 of the inner core 60 and a medial-most point 122 of an outer surface 92 of the shell 26. Each of the points 114, 116, 120, 122 lies in a common plane, as indicated by an imaginary line 126.

As shown in FIG. 3, the lateral thickness 110 is greater than the medial thickness 112. In other words, the combined thickness 110 of the shell 26 and the casing 24 on the lateral side 100 of the stem component 14 is greater than the combined thickness 112 of the shell 26 and the casing 24 on the medial side 98 of the stem component 14. In the illustrative embodiment, the lateral thickness 110 is greater than 5 millimeters, and the medial thickness 112 is greater than 2 millimeters.

The combined lateral thickness 110 includes a thickness 130 of the casing 24 and a thickness 132 of the shell 26. As shown in FIG. 3, the thickness 130 is defined between the lateral-most point 114 of the lateral surface 70 of the inner core 60 and a lateral-most point 134 of a lateral surface 136 of the casing 24. The lateral-most point 134 of the inner core 60 lies in the common plane with the other points 114, 116, 120, 122. The thickness 132 of the shell 26 is defined between the lateral-most point 134 of the lateral surface 136 of the casing 24 and the lateral-most point 116 of an outer surface 92 of the shell 26. In the illustrative embodiment, the lateral thickness 130 of the casing 24 is greater than the lateral thickness 132 of the shell 26.

Similarly, the combined medial thickness 112 includes a thickness 140 of the casing 24 and a thickness 142 of the shell 26. As shown in FIG. 3, the thickness 140 is defined between the medial-most point 120 of the medial surface 68 of the inner core 60 and a medial-most point 144 of a medial surface 146 of the casing 24. The medial-most point 144 of the inner core 60 lies in the common plane with the other points 114, 116, 120, 122, 134. The thickness 142 of the shell 26 is defined between the medial-most point 144 of the medial surface 146 of the casing 24 and the medial-most point 122 of an outer surface 92 of the shell 26. In the illustrative embodiment, the medial thickness 140 of the casing 24 is greater than the medial thickness 142 of the shell 26.

In the distal section 54 of the casing 24, the thickness of the casing 24 on the lateral side 100 of the stem component 14 is also greater than the thickness of the casing 24 on the medial side 98 of the stem component 14. For example, as shown in FIG. 4, casing 24 has a lateral thickness 150 and a medial thickness 152 when viewed in a transverse plane extending through the distal section 54. The lateral thickness 150 is defined between a lateral-most point 154 of the lateral surface 70 of the inner core 60 and a lateral-most point 156 of the outer surface 90 of the casing 24. The medial thickness 152 of the casing 24 is defined between a medial-most point 158 of the medial surface 68 of the inner core 60 and a medial-most point 160 of the surface 90 of the casing 24. As shown in FIG. 4, the lateral thickness 150 is greater than 4.5 millimeters. In that way, the lateral thickness 150 of the casing 24 is greater than the lateral thickness 130.

Returning to FIG. 2, the prosthesis 10 also includes a head component 12 that may be secured to the stem component 14. As described above, the head component 12 includes a tapered bore 22 that receives a tapered post 40 of the stem component 14. In the illustrative embodiment, the tapered bore 22 is defined in an insert 162 formed from a polymeric material such as, for example, polyetheretherketone ("PEEK") or polyetherketoneketone ("PEKK"). As shown in FIG. 2, the insert 162 includes the opening 20 defined in the distal surface 18 and an inner wall 164 extends inwardly from the opening 20 to define the bore 22. In that way, the composite tapered post 40 of the stem component 14 engages the polymeric insert 162 when the head component 12 is secured to the stem component 14.

The insert 162 is secured to a body 166 of the head component 12 formed from an implant grade metallic material such as, for example, cobalt-chromium alloy ("CoCr") or a titanium alloy such as Ti-6Al-4V. As shown in FIG. 2, the body 166 has an aperture 168 defined therein, and the insert 162 is positioned in the aperture 168. In the illustrative embodiment, the insert 162 is injection molded into the body 166. In other embodiments, the insert 162 may be formed separately from the body 166 and later secured to the body 166 via a locking device such as mechanical fixation. It should be appreciated that in other embodiments the head component 12 may be entirely formed from an implant grade metallic material.

In use, the prosthesis 10 is inserted into a proximal end of a patient's surgically-prepared femur. The elongated stem component 14 is received in the intramedullary canal and the casing 24 and the shell 26 engage the portion of the patient's femur surrounding the canal. As described above, the inner core 60 is sized and shaped to meet the minimum strength requirements of the prosthesis 10, while the casing 24 and the shell 26 cooperate to provide the stem component 14 with the external geometry necessary to fit into the intramedullary canal. The combination of the high tensile strength/high elastic modulus core 60 with the low modulus casing 24 and the low modulus shell 26 results in a reduced stiffness for the stem component 14 such that stress shielding of the patient's bone is reduced.

Figure 5:
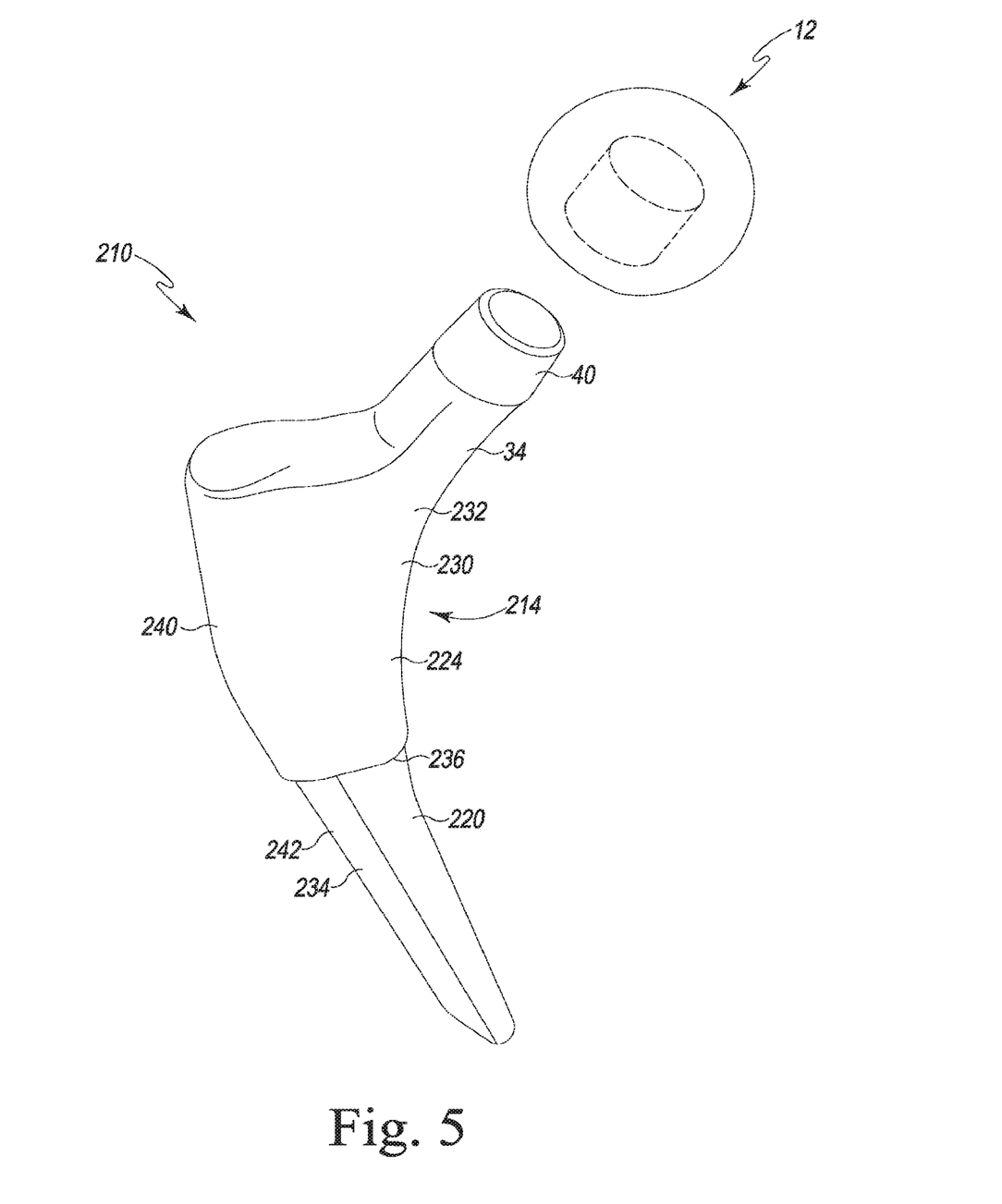
FIG. 5 is a perspective view of another embodiment of the implantable hip prosthesis.

Referring now to FIGS. 5-8, another embodiment of an implantable hip prosthesis (hereinafter prosthesis 210) is shown. The prosthesis 210 is similar to the prosthesis 10 described above in regard to FIGS. 1-4. As such, the same reference numbers will be used to identify features of the prosthesis 210 that are the same as those included in the prosthesis 10. The implantable hip prosthesis 210 (hereinafter prosthesis 210) includes a head component 12 and an elongated stem component 214 that is configured to be inserted into an intramedullary canal of a patient's surgically-prepared (e.g., reamed and/or broached) femur. As described above, the stem component may not include a metallic foam shell secured to the casing. As shown in FIG. 5, the stem component 214 includes a core 220 and a shell or casing 224 secured to the core 220. The stem component 214 does not include a metallic foam shell such that the core 220 and the casing 224 cooperate to define the external geometry of the stem component.

The casing 224 includes a neck 34 that is configured to be coupled to the head component 12. Like the embodiment of FIGS. 1-4, the neck 34 includes a tapered post 40 that is received in the tapered bore 22 of the head component 12. The casing 224 also includes a sheath 230 that extends distally from a proximal end 232 attached to the neck 34 and a cover layer 234 that extends distally from the sheath 230 to a distal end 236. In the illustrative embodiment, the neck 34, the sheath 230 and the cover layer 234 are formed as a monolithic structure. It should be appreciated that in other embodiments the components of the casing 224 may be formed as separate components. The separate components may be secured to one another by a mechanical fastener (e.g., screw, bolt, taper fit, etc.), adhesive, or other suitable fastener or secured separately to the core 220.

As shown in FIG. 5, the core 220 is sized and shaped to meet the minimum strength requirements of the prosthesis 10, while the casing 224 defines an external geometry of the stem component 14 necessary to fit into the intramedullary canal of the patient's femur. An exemplary core is described in U.S. Utility patent application Ser. No. 13/526,032 entitled "DUAL MODULUS HIP STEM AND METHOD OF MAKING THE SAME," which is expressly incorporated herein by reference. The core 220 is formed as a monolithic structure (e.g., a single molded or cast part). It should be appreciated that in other embodiments the components of the core 220 may be formed as separate components secured to one another by a mechanical fastener (e.g., screw, bolt, taper fit, etc.), adhesive, or other suitable fastener. The core 220 is formed from an implant grade metallic material having a high tensile strength and a high elastic modulus (i.e., a high material stiffness). In the illustrative embodiment, the core 220 is formed from cobalt-chromium alloy ("CoCr") having a minimum ultimate tensile strength of 650 MPa and an elastic modulus of approximately 195 GPa. It should be appreciated that in other embodiments the core 220 may be formed any material having a high tensile strength and a high elastic modulus, including, for example, a titanium alloy such as Ti-6Al-4V, which has a minimum ultimate tensile strength of 750 MPa and an elastic modulus of approximately 105 GPa.

In the illustrative embodiment, the casing 224 molded over the core 220. The casing 224 is formed from a composite reinforced polymer such as, for example, carbon-fiber reinforced polyetheretherketone ("PEEK"). The composite has an elastic modulus of approximately 21.5 GPa and an ultimate tensile strength of approximately 223 MPa. In that way, the casing 224 has an elastic modulus that is closer to that of a patient's femur. It should be appreciated that in other embodiments the casing 24 may be formed any composite or polymeric material having a low elastic modulus, such as, for example, a glass-filled polymer such as glass-filled PEEK, a non-reinforced polymer such as neat PEEK, or other reinforced or non-reinforced polymer.

As shown in FIG. 5, the sheath 230 of the casing 224 has an outer surface 240, and the cover layer 234 has an outer surface 242. The outer surfaces 240, 242 define a portion of the external geometry of the prosthesis 10. As such, the outer surfaces 240, 242 engage a portion of the patient's femur defining the intramedullary canal when the implant 10 is inserted into the proximal end of the patient's surgically-prepared femur. In the illustrative embodiment, the outer surface 240 of the sheath 230 is porous to enable bone ingrowth fixation, and the outer surface 242 of the cover layer 234 is non-porous. It should be appreciated that in other embodiments the cover layer 234 may also be porous.

Figure 6:
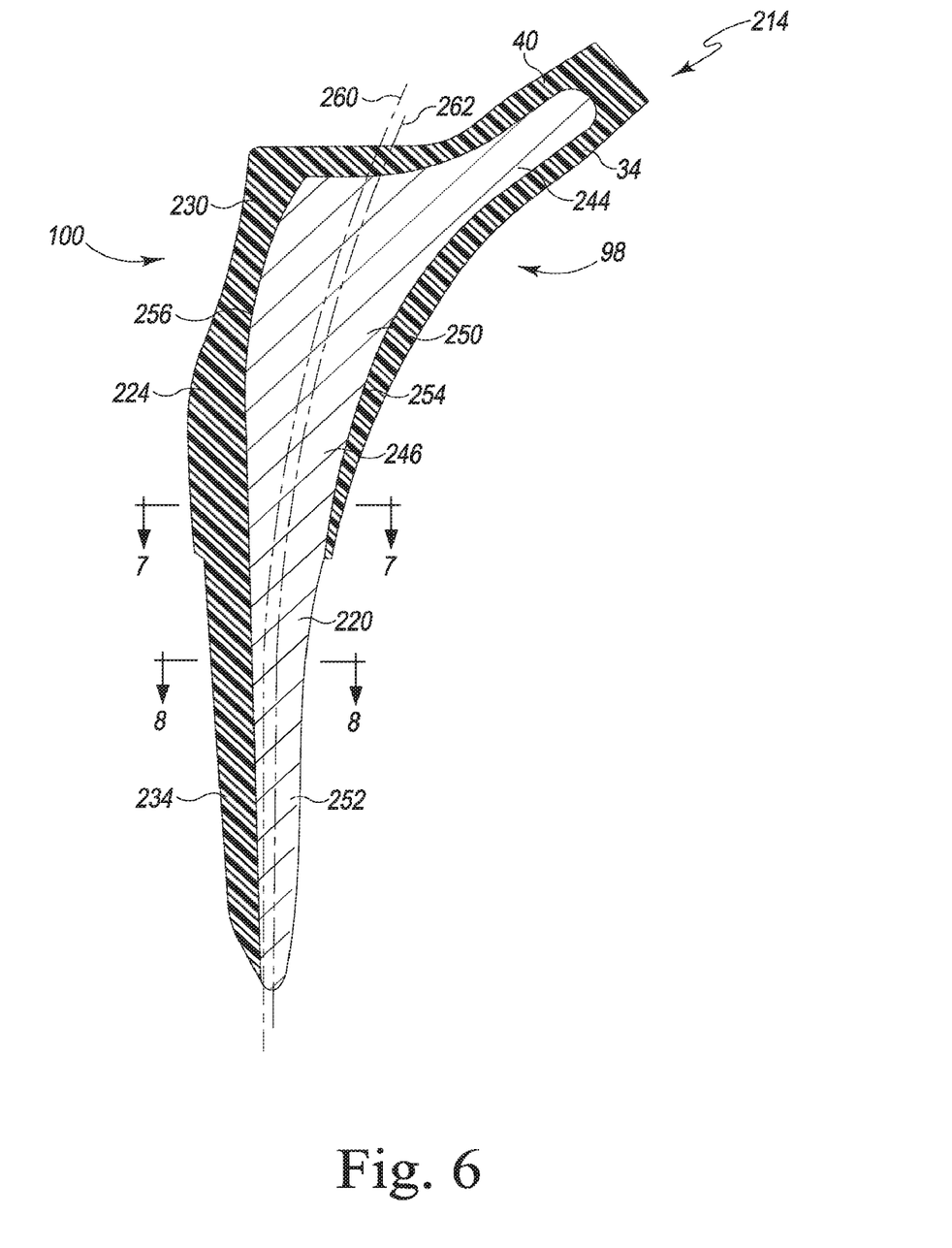
FIG. 6 is a cross-sectional elevation view of the implantable hip prosthesis of FIG. 5.

As shown in FIG. 6, the core 220 of the stem component 214 includes a proximal core body 244 and an elongated distal core body 246 extending from the proximal core body 244. The proximal core body 244 extends into the neck 34 of the casing 224 to reinforce the tapered post 40, while the elongated distal core body 246 extends through the sheath 230 of the casing 224. In the illustrative embodiment, the distal core body 246 includes a core segment 250 that is positioned in the sheath 230, and a core segment 252 that is positioned distal of the sheath 230. The sheath 230 is attached to and encases a medial surface 254 and a lateral surface 256 of the core segment 252.

The core body 246 (i.e., the core segments 250, 252) and the casing 224 (i.e., the sheath 230 and cover layer 234) cooperate to define a longitudinal axis 260 of the stem component 214. The core body 246 has a longitudinal axis 262. As shown in FIG. 6, the axis 262 is offset from the axis 260 in the medial direction such that the core body 246 is biased toward a medial side 98 of the stem component 214 and away from the lateral side 100 of the stem component 214. Additionally, the thickness of the casing 224 on the lateral side 100 of the stem component 214 is greater than the thickness of the casing 224 on the medial side 98 of the stem component 214.

Figure 7:
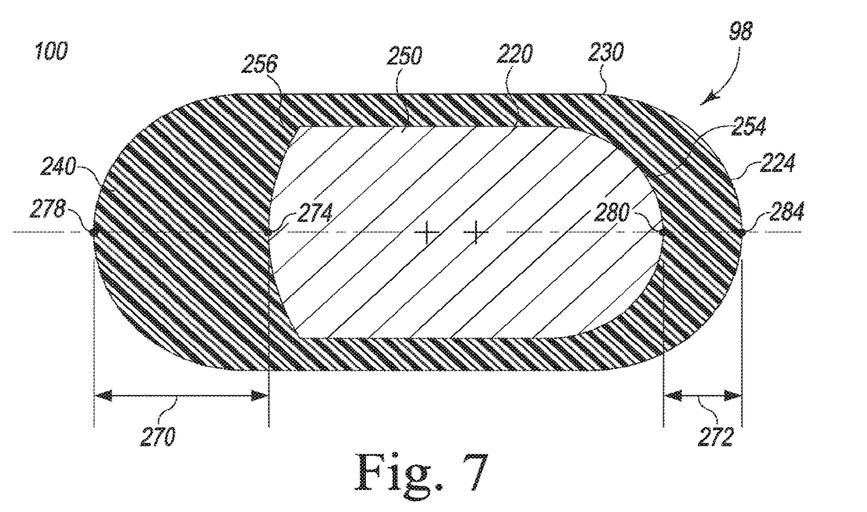
FIG. 7 is a cross-sectional view of the implantable hip prosthesis taken along the line 7-7 in FIG. 5.

For example, as shown in FIG. 7, the sheath 230 has a lateral thickness 270 and a medial thickness 272 when viewed in a transverse plane extending through the sheath 230 and the core segment 250. The lateral thickness 270 of the sheath 230 is defined between a lateral-most point 274 of the lateral surface 256 of the core segment 250 and a lateral-most point 278 of the outer surface 240 of the sheath 230. The medial thickness 272 of the sheath 230 is defined between a medial-most point 280 of a medial surface 254 of the core segment 250 and a medial-most point 284 of the outer surface 240 of the sheath 230. Each of the points 274, 278, 280, 284 lies in a common plane, as indicated by an imaginary line 286.

As shown in FIG. 7, the lateral thickness 270 is greater than the medial thickness 272. In other words, the thickness 270 of the casing 224 on the lateral side 100 of the stem component 214 is greater than the thickness 272 of the casing 224 on the medial side 98 of the stem component 214. In the illustrative embodiment, the lateral thickness 270 is greater than 5 millimeters, and the medial thickness 272 is between 2 and 4.5 millimeters.

Figure 8:
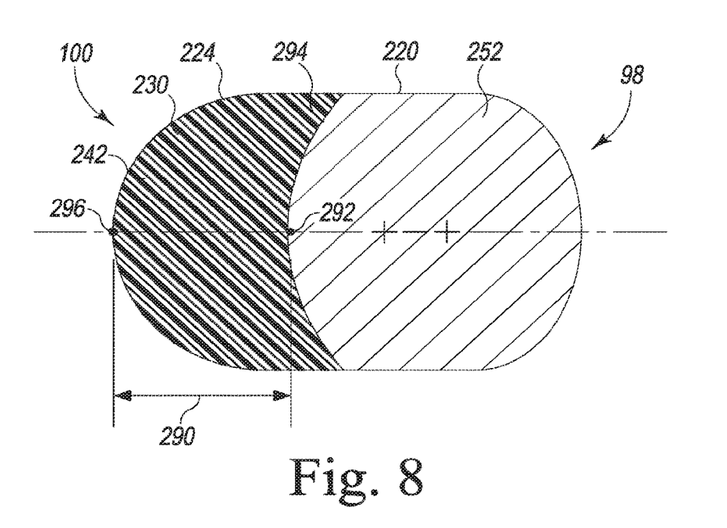
FIG. 8 is a cross-sectional view of the implantable hip prosthesis taken along the line 8-8 in FIG. 5.

In the illustrative embodiment, the cover layer 234 of the casing 224 decreases in thickness as it extends distally along the core segment 252. For example, as shown in FIG. 8, the cover layer 234 has a lateral thickness 290 when viewed in a transverse plane that extends through the cover layer 234 and the core segment 252. The lateral thickness 290 is defined between a lateral-most point 292 of a lateral surface 294 of the core segment 252 and a lateral-most point 296 of the outer surface 242 of the cover layer 234. As shown in FIG. 9, the lateral thickness 290 is greater than 4.5 millimeters.

In use, the prosthesis 210 is inserted into a proximal end of a patient's surgically-prepared femur. The elongated stem component 214 is received in the intramedullary canal and the sheath 230 and the cover layer 234 of the casing 224 engage the portion of the patient's femur surrounding the canal. As described above, the core 220 is sized and shaped to meet the minimum strength requirements of the prosthesis 210, while the casing 224 is configured to possess the external geometry necessary to fit into the intramedullary canal. The combination of the high tensile strength/high elastic modulus core 220 with the low modulus casing 224 results in a reduced stiffness for the prosthesis 210 such that stress shielding of the patient's bone is reduced.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of manufacturing an orthopaedic hip prosthesis comprising:
    forming a core from a material having a high tensile strength and a high elastic modulus, and
    attaching a polymeric shell to the core to position a proximal end of the core in a base of a tapered post of the polymeric shell, wherein attaching the polymeric shell includes placing a cover layer of the polymeric shell only on a lateral surface of a distal end of the core,
    wherein the tapered post of the polymeric shell extends from the base to a proximal tip, and the tapered post is sized to be received in a tapered bore of an implantable head component.

2. The method of claim 1, wherein attaching the polymeric shell includes:
    defining a first thickness of polymeric material between a medial-most point of the polymeric shell and a medial-most point of a medial surface of the core when viewed in a transverse plane, and
    defining a second thickness of polymeric material between a lateral-most point of the polymeric shell and a lateral-most point of a lateral surface of the core when viewed in a transverse plane,
    wherein the first thickness is less than the second thickness.

3. The method of claim 1, wherein forming the core includes forming a medial surface of the core such that the medial surface has a first radius when the orthopaedic hip prosthesis is viewed in the transverse plane, and forming a lateral surface of the core such that the lateral surface has a second radius greater than the first radius when the orthopaedic hip prosthesis is viewed in the transverse plane.

4. The method of claim 1, wherein forming the core includes forming the core from a cobalt-chromium alloy.

5. The method of claim 1, wherein forming the core includes forming the core from a titanium alloy.

6. The method of claim 1, further comprising securing the implantable head component to the tapered post.

7. A method of manufacturing an orthopaedic hip prosthesis comprising:
    forming a core from a material having a high tensile strength and a high elastic modulus, wherein forming the core includes forming a medial surface of the core such that the medial surface has a first radius when the orthopaedic hip prosthesis is viewed in the transverse plane, and forming a lateral surface of the core such that the lateral surface has a second radius greater than the first radius when the orthopaedic hip prosthesis is viewed in the transverse plane, and
    attaching a polymeric shell to the core to position a proximal end of the core in a base of a tapered post of the polymeric shell,
    wherein the tapered post of the polymeric shell extends from the base to a proximal tip, and the tapered post is sized to be received in a tapered bore of an implantable head component.

8. The method of claim 7, wherein attaching the polymeric shell includes:
    defining a first thickness of polymeric material between a medial-most point of the polymeric shell and a medial-most point of a medial surface of the core when viewed in a transverse plane, and
    defining a second thickness of polymeric material between a lateral-most point of the polymeric shell and a lateral-most point of a lateral surface of the core when viewed in a transverse plane,
    wherein the first thickness is less than the second thickness.

9. The method of claim 7, wherein forming the core includes forming the core from a cobalt-chromium alloy.

10. The method of claim 7, wherein forming the core includes forming the core from a titanium alloy.

11. The method of claim 7, further comprising securing the implantable head component to the tapered post.

* * * * *